United States Patent [19]

Karami

[11] 4,029,100

[45] June 14, 1977

[54] SHAPE RETAINING DIAPER

[75] Inventor: Hamzeh Karami, Crystal Lake, Ill.

[73] Assignee: Colgate-Palmolive Company, New York, N.Y.

[22] Filed: Jan. 5, 1976

[21] Appl. No.: 646,702

[52] U.S. Cl. .............................. 128/284; 128/287; 128/296

[51] Int. Cl.² ....................................... A61F 13/16

[58] Field of Search .............. 128/284, 287, 290 R, 128/296

[56] References Cited

UNITED STATES PATENTS

| 3,071,138 | 1/1963 | Garcia | 128/290 R |
|---|---|---|---|
| 3,115,877 | 12/1963 | Harwood | 128/290 R |
| 3,371,667 | 3/1968 | Morse | 128/290 R |
| 3,431,911 | 3/1969 | Meisel, Jr. | 128/287 |
| 3,763,502 | 10/1973 | Laumann | 128/284 X |
| 3,769,978 | 11/1973 | DeNight | 128/287 |
| 3,812,001 | 5/1974 | Ryan | 128/284 |
| 3,816,227 | 6/1974 | Schaar | 128/285 X |
| 3,848,598 | 11/1974 | Mesek | 128/287 |
| 3,848,599 | 11/1974 | Schaar | 128/287 |
| 3,865,112 | 2/1975 | Roeder | 128/290 R |
| 3,888,257 | 6/1975 | Cook | 128/296 |

FOREIGN PATENTS OR APPLICATIONS

| 21,746 | 10/1902 | United Kingdom | 128/284 |

Primary Examiner—Aldrich F. Medbery
Attorney, Agent, or Firm—Powell L. Sprunger

[57] ABSTRACT

A disposable diaper comprising, an absorbent pad assembly having a pair of waistline portions, a crotch portion intermediate the waistline portion, a backing sheet, a fluid pervious cover sheet, and absorbent pad means positioned between the backing and cover sheets. The pad means comprises a first absorbent pad including a hydrophilic material and defining a front surface of the pad means between the crotch portion and waistline portions of the pad assembly, and a second pad in the crotch portion of a material which has a large wet resiliency relative the first pad to maintain the shape of the crotch portion when wetted and placed under loads during use of the diaper.

16 Claims, 4 Drawing Figures

SHAPE RETAINING DIAPER

BACKGROUND OF THE INVENTION

The present invention relates to absorbent articles, and more particularly to disposable diapers.

In the past, an assortment of disposable diapers have been proposed for use on infants. The diapers normally have a fluid impervious backing sheet, a fluid pervious cover sheet, and an absorbent pad positioned intermediate the backing and cover sheets. More commonly, the diaper pads are made from comminuted wood pulp, known in the art as wood fluff.

Although in many respects satisfactory for their intended purposes, the fibers of such pads have relatively low wet resiliency and collapse when wetted and placed under loads. Thus, during use of the diaper the crotch portion of such pads become soft and collapses when wetted, resulting in a deformed pad of relatively small volume in the crotch portion which does not adequately maintain its shape and cover the infant.

SUMMARY OF THE INVENTION

A principal feature of the present invention is the provision of a disposable diaper which performs in an improved manner when wetted and placed under loads.

The diaper of the present invention comprises, an absorbent pad assembly having a pair of waistline portions, a crotch portion intermediate the waistline portions, a backing sheet, a fluid pervious cover sheet, and absorbent pad means positioned between the backing and cover sheets. The pad means comprises a first absorbent pad including a hydrophilic material and defining a front surface of the pad means between the crotch portion and waistline portions of the pad assembly. The pad means has a second pad in the crotch portion of a material which has a large wet resiliency relative the first pad.

A feature of the present invention is that the second pad prevents collapse of the pad means in the crotch portion when the pad means is wetted and placed under loads.

Thus, another feature of the invention is that the second pad maintains the shape of the pad assembly in the crotch portion during use of the diaper.

Yet another feature of the invention is that in a preferred form the first pad comprises a comminuted wood pulp.

Still another feature of the invention is that the second pad may be made of a foam material.

Further features will become more fully apparent in the following description of the embodiments of this invention and from the appended claims.

DESCRIPTION OF THE PREFERRED EMBODIMENTS

Figure 1:
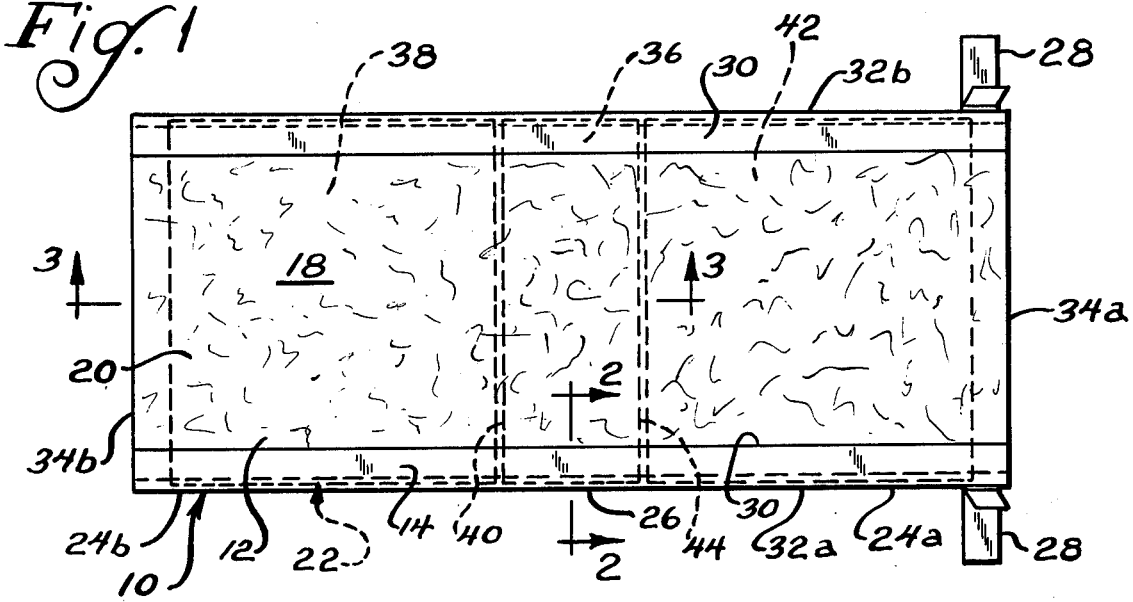
FIG. 1 is a plan view of a disposable diaper of the present invention.
Figure 2:
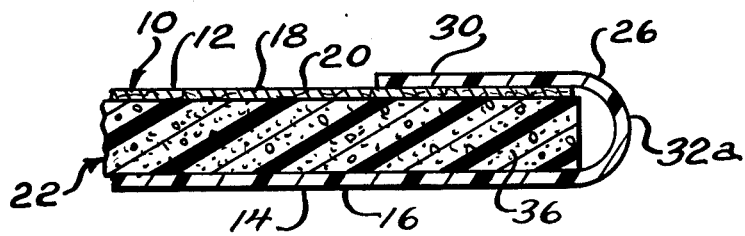
FIG. 2 is a fragmentary sectional view taken substantially as indicated along the line 2—2 of FIG. 1.
Figure 3:
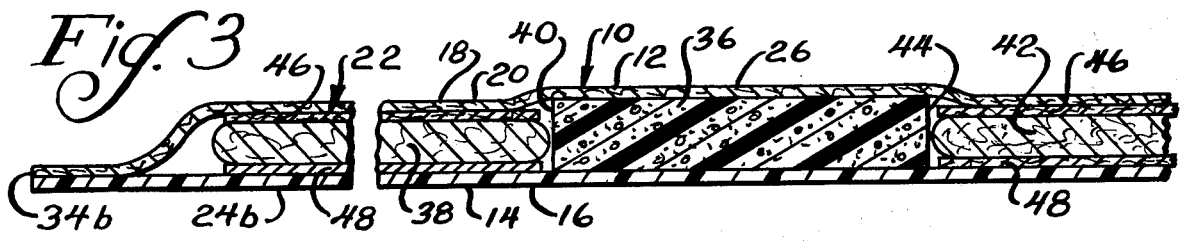
FIG. 3 is a fragmentary sectional view taken substantially as indicated along the line 3—3 of FIG. 1.

Referring now to FIGS. 1–3, there is shown a disposable diaper generally designated 10 having an absorbent pad assembly 12. The pad assembly 12 has a fluid impervious backing sheet 14, such as polyethylene, defining a back surface 16 of the pad assembly 12, a fluid pervious cover or top sheet 18, such as a nonwoven material, defining a front surface 20 of the pad assembly 12, and absorbent pad means generally designated 22 positioned intermediate the backing sheet 14 and cover sheet 18. Referring to FIG. 1, the pad assembly 12 has a pair of opposed waistline portions 24a and 24b, a crotch 26 located intermediate the waistline portions 24a and b, a pair of side edges 32a and 32b, and a pair of end edges 34a and 34b connecting the side edges 32a and b. The pad assembly 12 may also have a pair of conventional tape fasteners 28 for securing the diaper about an infant during placement of the diaper. With reference to FIGS. 1 and 2, the fluid impervious backing sheet 14 may have lateral side margins 30 which are folded over and secured to the cover sheet 18 above the pad means 22.

Referring to FIGS. 1–3, the pad means 22 has a first pad 36 of a foam material in the crotch portion 26 of the pad assembly 12, a second pad 38 of a hydrophilic absorbent material, such as comminuted wood pulp, located between a longitudinal side 40 of the first pad 36 and the end edge 34b of the pad assembly 12, and a third pad 42 of hydrophilic absorbent material, such as comminuted wood pulp, located between the other side 44 of the first pad 36 and the other end edge 34a of the pad assembly 12. Accordingly, the second and third pads 38 and 42 are located on opposed longitudinal sides of the first pad 36, such that they extend into the waistline portions 24a and b of the pad assembly 12, and define front surfaces of the pad means 22 on opposed longitudinal sides of the crotch portion 26. As best shown in Fig. 3, the second and third pads 38 and 42 may both include front and back wadding sheets 46 and 48, respectively, to maintain the structural integrity of the second and third pads and prevent balling of the pads during use.

The first pad 36 preferably extends the width of the pad means 22, and may be made of any suitable material having a relatively large wet resiliency, such as polyurethane foam or polyethylene foam. Also, as shown in FIG. 3, the first pad 36 preferably has a greater thickness than the thickness of the second and third pads 38 and 42.

During the use of the diaper, urine passes through the cover sheet 28 into the foam pad 36, and subsequently from the foam pad 36 into the spaced second and third pads 38 and 42 for retention therein. Due to the large wet resiliency of the foam pad 36, the pad 36 compresses, but does not collapse, when wetted and placed under loads. Accordingly, the foam pad recovers and retains its shape as the infant moves its legs, and the pad 36 maintains the desired shape of the diaper in the crotch portion 26 during use of the diaper when wetted and placed under loads.

Figure 4:
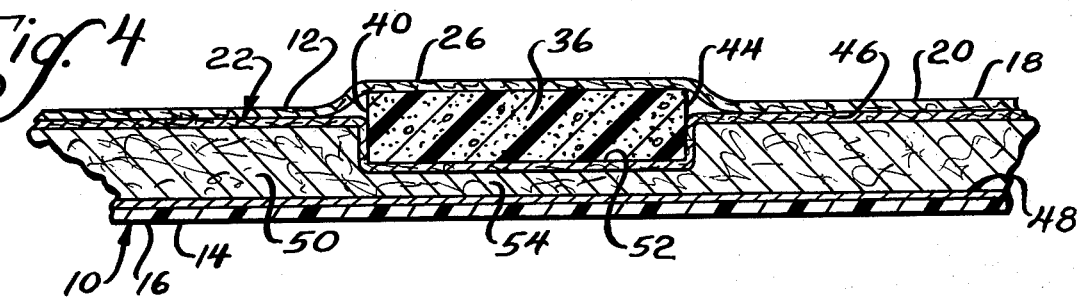
FIG. 4 is a fragmentary sectional view of another embodiment of the diaper of the present invention.

Another embodiment of the diaper of the present invention is illustrated in FIG. 4, in which like reference numerals designate like parts. In this embodiment, the pad means 22 also has a first pad 36 of a foam material located in the crotch portion 26 of the pad assembly 12. The pad means 22 has a second pad 50 of hydrophilic absorbent material, such as comminuted wood pulp, extending substantially between the waistline portions of the pad assembly, and defining front surfaces of the pad means 22 on opposed longitudinal sides 40 and 44 of the first pad 36 between the crotch portion 26 and waistline portions of the diaper. The second pad 50 may include front and back wadding sheets 46 and 48 to provide structural integrity for the pad, as previously described. The second pad 50 also has a cut-out or recess 52 in the crotch portion 26 to receive and retain the first foam pad 36 over a part 54 of the second pad 50 in the crotch portion 26 of the pad assembly. Accordingly, the first pad 36 is retained in place in the recess 52 of the second pad 50, and the first pad 36 maintains the shape of the pad assembly 12 in the crotch portion 26 when the diaper is wetted and placed under loads, in a manner as previously described in connection with the diaper of FIGS. 1–3. In a preferred form, the pad 36 projects above the front surfaces of the second pad 50 on opposed longitudinal sides of the first pad 36, as shown, such that the thickness of the pad means 22 in the crotch portion 26 of the pad assembly is greater than the thickness of the pad means intermediate the crotch portion and the waistline portion of the diaper.

The foregoing detailed description is given for clearness of understanding only and no unnecessary limitations should be understood therefrom as modifications will be obvious to those skilled in the art.

I claim:

1. A disposable diaper comprising, an absorbent pad assembly having a pair of waistline portions, a crotch portion intermediate said waistline portions, a backing sheet, a fluid pervious cover sheet, and absorbent pad means positioned between the backing and cover sheets, said pad means comprising a first absorbent pad including a hydrophilic material and defining a front surface of the pad means between the crotch portion and waistline portions of the pad assembly, and a second pad in said crotch portion of a material which has a large wet resiliency relative said first pad to maintain the shape of said crotch portion when wetted and placed under loads during use of the diaper.

2. The diaper of claim 1 wherein said first pad comprises comminuted wood pulp.

3. The diaper of claim 2 wherein said first pad includes a front wadding sheet defining said front surface.

4. A diaper of claim 1 wherein said second pad comprises a foam material.

5. The diaper of claim 4 wherein said second pad is made from a material selected from the group consisting of polyurethane foam, and polyethylene foam.

6. The diaper of claim 1 wherein said second pad extends substantially the width of said pad means.

7. The diaper of claim 1 wherein said pad means has a greater thickness in the crotch portion than adjoining areas of the pad means.

8. The diaper of claim 1 wherein said second pad projects above the front surface of the first pad.

9. A disposable diaper comprising, an absorbent pad assembly having a pair of waistline portions, a crotch portion intermediate said waistline portions, and absorbent pad means comprising, a first pad of foam material in said crotch portion, and a second pad including comminuted wood pulp and defining a front surface of the pad means on opposed longitudinal sides of the first pad.

10. A disposable diaper comprising, an absorbent pad assembly having a pair of waistline portions, a crotch portion intermediate said waistline portions, and absorbent pad means comprising, a first pad of a foam material in said crotch portion, and spaced second and third pads of an absorbent material located intermediate said first pad and the opposed waistline portions of the pad assembly.

11. The diaper of claim 10 wherein said second and third pads comprise comminuted wood pulp.

12. The diaper of claim 10 wherein the thickness of said first pad is greater than the thickness of said second and third pads.

13. A disposable diaper comprising, an absorbent pad assembly having a crotch portion, a pair of waistline portions, and absorbent pad means comprising, a first pad of an absorbent material, and a second pad of a foam material covering a part of said first pad only in the crotch portion of the pad assembly, with portions of said first pad defining a front surface of the pad means in both wasitline portions of the diaper.

14. The diaper of claim 13 wherein said first pad comprises comminuted wood pulp.

15. The diaper of claim 13 wherein said first pad includes a recess in its front surface to receive and retain said second pad in said pad means.

16. The diaper of claim 13 wherein said second pad projects above a front surface of the first pad defined between said second pad and the opposed waistline portions of the pad assembly.

* * * * *